US006702851B1

(12) United States Patent
Chinn et al.

(10) Patent No.: US 6,702,851 B1
(45) Date of Patent: Mar. 9, 2004

(54) PROSTHETIC HEART VALVE WITH SURFACE MODIFICATION

(76) Inventors: Joseph A. Chinn, 5006 Woodview Ave., Austin, TX (US) 78756; Jack R. Frautschi, 1107 Meadow Dr., Athens, TX (US) 78751; Richard E. Phillips, 129 Quail Creek Dr., San Marcos, TX (US) 78666

( * ) Notice: Subject to any disclaimer, the term of this patent is extended or adjusted under 35 U.S.C. 154(b) by 0 days.

(21) Appl. No.: 09/040,914

(22) Filed: Mar. 18, 1998

Related U.S. Application Data

(63) Continuation-in-part of application No. 08/711,431, filed on Sep. 6, 1996, now abandoned.

(51) Int. Cl.$^7$ .................................................. A61F 2/24
(52) U.S. Cl. ..................... 623/2.1; 623/2.12; 623/2.2; 623/11.11; 427/2.24
(58) Field of Search ................................. 623/2, 11, 66, 623/901, 2.1, 2.12, 2.2, 11.11; 427/2.24; 523/113

(56) References Cited

U.S. PATENT DOCUMENTS

| 3,954,583 A | | 5/1976 | Lednicer et al. ......... 204/158 R |
| 4,363,142 A | * | 12/1982 | Meyer ............................. 623/2 |
| 4,364,127 A | | 12/1982 | Pierce et al. ..................... 3/1.5 |
| 4,979,959 A | * | 12/1990 | Guire ............................. 623/66 |
| 5,002,582 A | * | 3/1991 | Guire ............................. 623/66 |
| 5,017,670 A | | 5/1991 | Frautschi et al. ............ 527/313 |
| 5,019,393 A | | 5/1991 | Ito et al. ....................... 424/423 |
| 5,098,960 A | | 3/1992 | Frautschi ................... 525/359.3 |
| 5,098,977 A | | 3/1992 | Frautschi et al. ............ 527/313 |
| 5,112,615 A | | 5/1992 | Ito et al. ....................... 424/426 |
| 5,126,140 A | | 6/1992 | Ito et al. ....................... 424/423 |
| 5,167,960 A | | 12/1992 | Ito et al. ....................... 424/423 |
| 5,263,992 A | * | 11/1993 | Guire ............................. 623/66 |
| 5,509,932 A | | 4/1996 | Keogh et al. .................. 623/11 |
| 5,554,184 A | * | 9/1996 | Machiraju ........................ 623/2 |

OTHER PUBLICATIONS

Rittenhouse, E.A. et al, Heparin–bound Aminoethycellulose as an Antithrombogenic Surface, Arch Surg, 1972, vol. 105, pp. 752–755.
Chinn, J.A. et al, Comparison of In Vitro and In Vivo Bio Stability of Surface Modification Polymers as Determined by Radiolabel, 9/95, Surface in Biomaterials Foundation, pp. 176–181.
Frautschi, J.R. et al., Surface Modification of Prototype Polymer Valves Improves Valve Performance in the Ovine Mitral Model, Surfaces in Biomaterials Foundations, 9/95, pp. 116–120.
Ishihara, T., et al. Calcific Deposits Developing in a Bovine Pericardial Bioprosthetic Valve 3 Days After Implantation, Circulation vol. 63, No. 3, 3/81, pp. 718–723.
Schoen, F.J. et al., Biomaterial–Associated Calcification: Pathology, Mechanisms, and Strategies for Prevention, Biomaterial Associated Calcification, pp. 11–36.
Chinn, J. A., A New Generation of Heart Valve, Sulzer Technical Review 4/96, pp. 34–35.

* cited by examiner

Primary Examiner—Dinh X. Nguyen

(57) ABSTRACT

A biocompatible heart valve is described having incorporated therein an effective amount of applied coating to render the valve resistant to in vivo pathologic thrombus formation and resistant to in vivo pathologic calcification.

4 Claims, 7 Drawing Sheets

(7 of 7 Drawing Sheet(s) Filed in Color)

HP-100/³H-FA
Fatty Acid Modified SR

JFV66 (157d)    JFV67 (156d)    JFV69 (151d)

High performance silicone rubber valves, surface modified with FA-1, retrieved after 5 month ovine mitral implant.

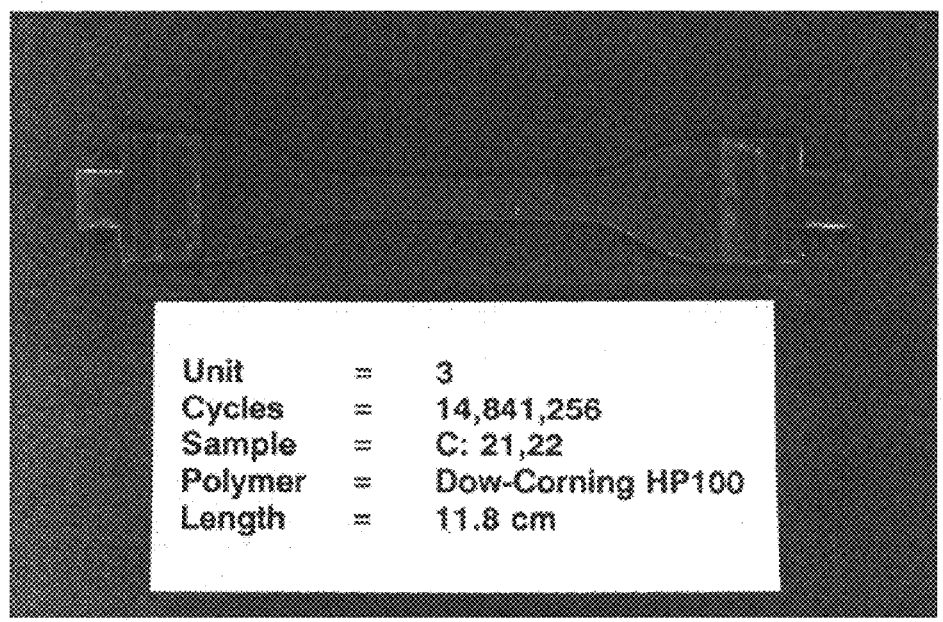
Figure 1: Photograph of HP100 sample after 12 weeks incubation under cyclic strain in calcium and phosphate supplemented, heparinized, bovine plasma.

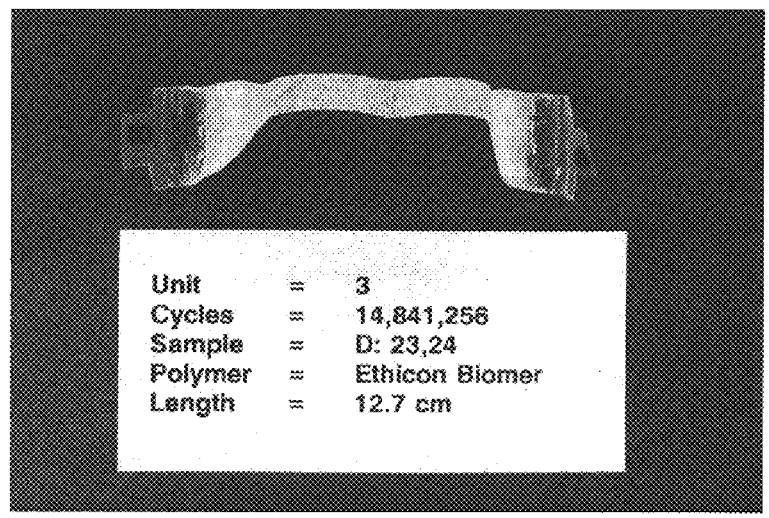
Figure 2: Photograph of Ethicon biomer sample after 12 weeks incubation under cyclic strain in calcium and phosphate supplemented, heparinized, bovine plasma.

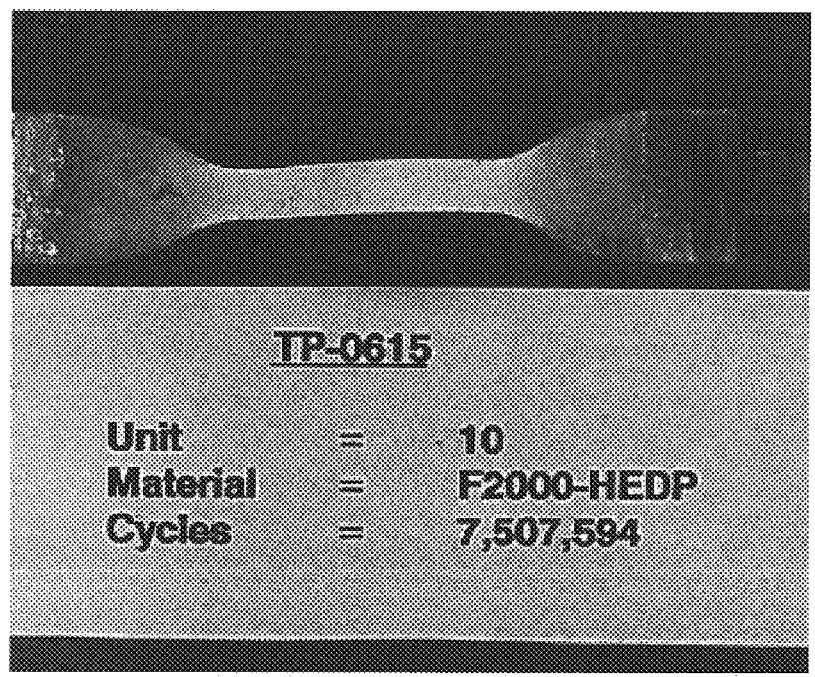
Figure 3: Photograph of F2000-HEDP after 6 weeks incubation under cyclic strain.

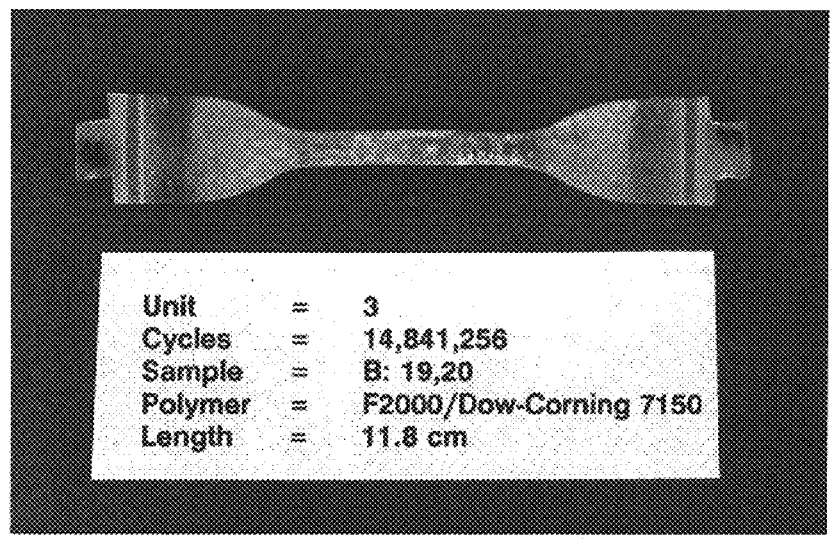
Figure 4: Photograph of F2000/Dow Corning 7150 sample after 12 weeks incubation under cyclic strain in calcium phosphate supplemented, heparinized, bovine plasma.

HP-100/ ³H-HA
Hyaluronic Acid Modified SR
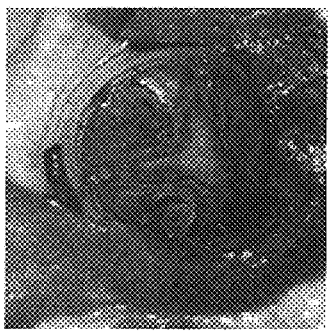  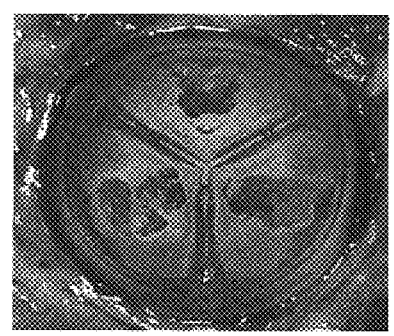
JFV61 (151d)　　　JFV62 (151d)　　　JFV64 (155d)
Figure 5: High performance silicone rubber valves surface modified with HA-1, retrieved after 5 month ovine mitral implant.

HP-100/³H-FA
Fatty Acid Modified SR
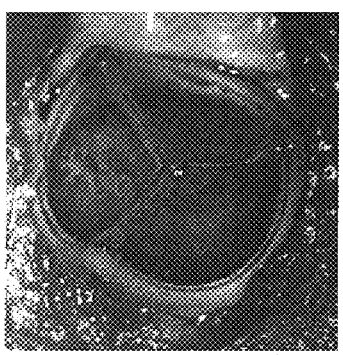 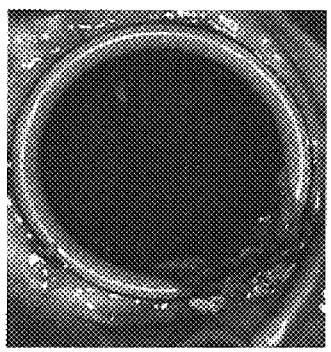 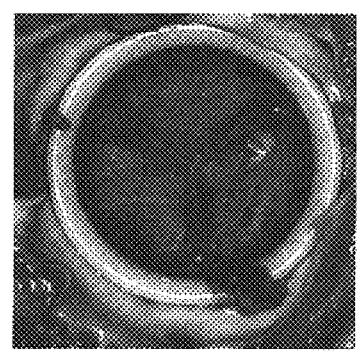
JFV66  JFV67  JFV69
(157d)  (156d)  (151d)
Figure 6: High performance silicone rubber valves, surface modified with FA-1, retrieved after 5 month ovine mitral implant.

HP-100 Silicone Rubber
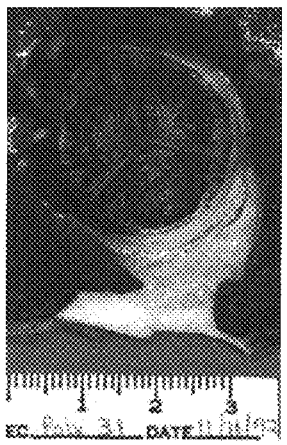
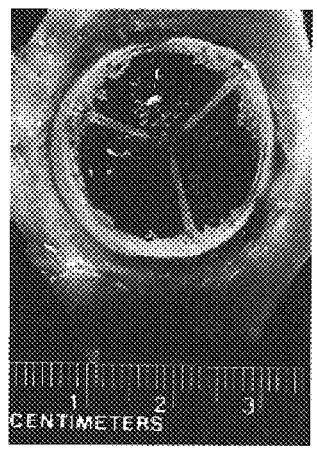
POLY30 (delamination leak, 127d)    POLY31 (147d)    POLY32 (147d)
Figure 7: Photographs of high performance silicone rubber valves retrieved after 5 month ovine mitral implant.

PROSTHETIC HEART VALVE WITH SURFACE MODIFICATION

The present application is a continuation-in-part of U.S. patent application Ser. No. 08/711,431, filed Sep. 6, 1996, now abandoned. The entire text of the prior application is specifically incorporated herein in its entirety.

The present invention relates to biocompatible heart valves having increased resistance to calcification and thrombus formation. The heart valves of the present invention include an effective amount of thrombus inhibiting and calcification inhibiting coating.

In particular, the heart valves of the present invention have incorporated therein an effective amount of applied coating to render the valve resistant to in vivo pathologic thrombus formation and resistant to in vivo pathologic calcification. The subject invention also features a novel method for manufacturing heart valves having a thrombus resistant and calcification resistant coating.

BACKGROUND OF THE INVENTION

The continuing advances in the design of heart valves prostheses and techniques for their implantation have produced impressive results in the length and quality of survival in patients who receive these devices. With the ever increasing effort to develop a more durable and compatible heart valve prosthesis, basic and clinical scientists have used a wide and varied number of techniques to determine the suitability of given valve materials for a given implant application. These techniques, aimed at determining the implant/host interaction, have generally been included under the term "biocompatibility". Investigators commonly deal with biocompatibility in terms of whether the implant material or its degradation products, if any, initiate adverse tissue responses in the host or conversely whether deleterious changes in the chemical, physical and/or mechanical properties of the implant material are caused by the host environment. The vast majority of fundamental studies of biocompatibility involve animal models. The ultimate test for biocompatibility of a polymer, device or prosthesis, is human implantation.

Prosthetic heart valves in clinical use today are of two varieties, mechanical and tissue. Mechanical heart valves are very durable, but their use is complicated by thromboembolism, hemorrhage, and hemolysis. Tissue valves require no chronic anticoagulation of the patient but often fail due to calcification and tissue tearing. Potential alternative materials that are sufficiently durable and blood compatible for use in a prosthetic heart valve device include non-glutaraldehyde fixed bovine pericardial tissue, which has been observed in the ovine mitral model to calcify less than does glutaraldehyde fixed tissue, and synthetic polymers such as polyurethanes, which have been reported in many different models to also calcify less than does glutaraldehyde fixed bovine pericardial tissue.

This invention relates generally to biocompatible heart valves which are resistant to in vivo calcification, and more particularly, to calcification-resistant and thrombus resistant heart valves comprising synthetic polymers or materials of natural origin, such as bovine pericardium, porcine heart valves or homografts, having incorporated therein an effective amount of a coating to impart resistance to calcification and impart resistance to thrombus formation.

The precise mechanism for pathological calcification of cardiovascular tissue is not well understood. Generally, the term "pathologic calcification" refers to the deposition of calcium phosphate mineral salts in association with a disease process. See Schoen et. al, "Biomaterial-associated calcification: Pathology, mechanisms, and strategies for prevention", J. Biomed. Mater. Res.: Applied Biomaterials, Vol. 22 A1, 11–36 (1988), incorporated herein by reference. Calcification may be due to host factors, implant factors, and extraneous factors such as mechanical stress. There is some evidence to suggest that calcium deposits are related to devitalized cells, especially membrane cells, where the calcium pump ($Ca^{+2}$-$Mg^{+2}$-ATPase) responsible for maintaining low intracellular calcium levels is weakened or no longer functioning. Calcification has been observed to begin with an accumulation of calcium and phosphorous, present as hydroxyapatite, which develops into nodules which can eventually lead to a valvular failure.

The location of calcific sites on a heart valve prothesis may be intrinsic, i.e., within the boundaries of the biomaterials of the prosthesis, or extrinsic, i.e., outside of the biomaterials, perhaps attached to the valve prosthesis, e.g., within thrombus or other pseudointima. Extrinsic calcification itself rarely causes failure of bioprosthetic valves; the predominant calcific deposits responsible for bioprostietic valve failure are intrinsic. With polymer valves it is believed that both intrinsic and extrinsic calcification must be controlled. Therefore a biocompatible heart valve prosthesis is needed that is resistant not only to thrombus formation, but also to calcification, particularly intrinsic calcification.

SUMMARY OF THE INVENTION

In its broad embodiment, the present invention is directed to a biocompatible heart valve having incorporated therein an effective amount of applied coating to render said heart valve resistant to in vivo pathologic thrombus formation and resistant to in vivo pathologic calcification.

The instant invention is also directed to a bioprosthetic heart valve comprising: a stent defining a blood flow path; and a plurality of leaflets, each of said leaflets having incorporated therein an effective amount of a photochemically applied coating to render said heart valve resistant to in vivo pathologic thrombus formation and resistant to in vivo pathologic calcification.

In another aspect, the present invention relates to a polymeric bioprosthetic heart valve comprising: a stent defining a blood flow path; and a plurality of polymeric based leaflets, each of said leaflets having incorporated therein an effective amount of a applied coating to render said heart valve resistant to in vivo pathologic thrombus formation and resistant to in vivo pathologic calcification.

The instant invention is also directed to a bioprosthetic heart valve comprising: a stent defining a blood flow path; and a plurality of silicone rubber leaflets, each of said leaflets having incorporated therein an effective amount of a photochemically applied coating to render said heart valve resistant to in vivo pathologic thrombus formation and resistant to in vivo pathologic calcification.

The invention also provides a bioprosthetic heart valve comprising: a stent defining a blood flow path; and a plurality of phosphonate modified polyetherurethane leaflets, each of said leaflets further having incorporated therein an effective amount of a photochemically applied coating to render said heart valve resistant to in vivo pathologic thrombus formation and resistant to in vivo pathologic calcification.

The coatings that are effective to achieve resistance to in vivo thrombus formation and resistance to in vivo pathologic calcification are derived from photochemically activated precursors. Generally the coatings are derived from precursors of the general formula:

X-Y-Z wherein X is a photochemically reactive group capable upon activation of bonding to the surface of the heart valve; Y represents nothing or a relatively inert, noninterfering skeletal moiety joining group X and is resistant to cleavage in aqueous physiological fluids and Z represents a functionally active moiety or biocompatible agent. The noninterfering skeletal moiety of Y may include an alkyl chain ($C_1$–$C_{10}$) or PEO (polyethylene oxide) (MW=200–1450).

The biocompatible heart valves of the present invention can be made of a biomaterial selected from the group consisting of natural tissue and biocompatible synthetic polymer. The natural tissue biomaterial is typically selected from the group consisting of bovine pericardium tissue and porcine tissue while the synthetic polymeric material is an organic synthetic material selected from the group consisting of siloxane polymers, polydimethylsiloxanes, silicone rubbers, polyurethane, polyether urethane, polyesterurethane, polyamide, polycarbonate, polyester, polypropylene, polyethylene, polystyrene, polyvinyl chloride, polytetrafluoroethylene, polysulfone, cellulose acetate, polymethylmethacrylate, and poly(ethylene/vinylacetate).

In the practice of the present invention, the valves are fabricated by dissolving the polymer in an appropriate solvent, and then a hard polymer stent is repeatedly dipped into the polymer solution and then dried. The coated stent is then placed over a leaflet mandrel, which is then dipped a predetermined number of times into the solution to provide valve leaflets of the desired thickness. The valves are typically of the multi-leaflet design. For surface modification, the valves are modified by dipping in the appropriate chemical solution or spraying appropriate chemical solution, and then exposed to light of a given wavelength so as to deposit the coating. The coating process can be repeated several times as desired.

The biocompatible polymer valves of the present invention are typically of the tri-leaflet design, which are similar to the design of bioprosthetic valves used clinically. To minimize residual stresses, a hard polymer stent is repeatedly dipped into a polymer solution, and the cast polymer is then heat cured. The valves are surface modified to improve the blood compatibility of the base polymer.

The present invention further provides a method for reducing calcification and thrombus formation in bioprosthetic heart valves after implantation in an animal comprising: coating, prior to implantation, said heart valves including its leaflets with a coating derived from a compound of the formula

X-Y-Z wherein X is a photochemically reactive group capable upon activation of bonding to the surface of the heart valve; Y represents nothing or a relatively inert, noninterfering skeletal moiety joining group X and is resistant to cleavage in aqueous physiological fluids and Z represents a functionally active moiety or biocompatible agent. The noninterfering skeletal moiety of Y may include an alkyl chain ($C_1$–$C_{10}$) or PEO (MW=200–1450), said coating being in an effective amount to reduce calcification and thrombus formation after implantation.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

The invention may be best understood by reference to the following description taken in conjunction with the accompanying drawings, in which:

FIG. 1 is a photograph of HP100 sample after 12 weeks incubation under cyclic strain in calcium and phosphate supplemented, heparinized bovine plasma.

FIG. 2 is a photograph of Ethicon biomer sample after 12 weeks incubation under cyclic strain in calcium and phosphate supplemented, heparinized bovine plasma.

FIG. 3 is a photograph of F2000-HEDP after 6 weeks incubation under cyclic strain.

FIG. 4 is a photograph of F2000/Dow Corning 7150 sample after 12 weeks incubation under cyclic strain in calcium and phosphate supplemented, heparinized bovine plasma.

FIG. 5 is a photograph of silicone rubber valves which have been surface modified with HA-1, retrieved 5 months after implantation.

FIG. 6 is a photograph of silicone rubber valves which have been surface modified with FA-1, retrieved 5 months after implantation.

FIG. 7 is a photograph of silicone rubber valves which have not been surface modified, retrieved 5 months after implantation.

DESCRIPTION OF THE PREFERRED EMBODIMENT

The following embodiment of the present invention provides biocompatible heart valves having improved resistance to calcification and improved resistance to thrombus formation which can be implanted in a an animal or human being. The valves include a coating of a biocompatible material which can be applied by photochemical activation. The coatings may be covalently or non-covalently coated or a combination of both. The coating whether covalently bonded or non-covalently bonded or both when incorporated into the heart valve including its leaflets is intended to provide anticalcification and antithrombus effects over a sustained period of time. The biocompatible coatings of the present invention are typically derived from materials that are also compatible with the materials of construction used to make the heart valves whether natural or synthetic.

The materials of choice should be compatible with all fluids of the human body i.e., when implanted in the body of a human being, it is biologically inert, physiologically acceptable, non-toxic, and insoluble in the environment of use. The materials are typically naturally derived or they are based on synthetic organic polymers which are biocompatible.

The biocompatible synthetic polymer is typically an organic synthetic material selected from the group consisting of siloxane polymers, polydimethylsiloxanes, silicone rubbers, polyurethane, polyether urethane, polyesterurethane, polyamide, polycarbonate, polyester, polypropylene, polyethylene, polystyrene, polyvinyl chloride, polytetrafluoroethylene, polysulfone, cellulose acetate, polymethylmethacrylate, and poly(ethylene/vinylacetate). The tissue biomaterial is selected from the group consisting of bovine pericardium tissue and porcine tissue.

A preferred material for use in the practice of the present invention is a high performance silicon rubber manufactured by Dow Corning, Midland, Mich. (designated herein after as HP-100). The above silicone rubber is characterized as a Platinum catalystized silicon elastomer made from dimethylsiloxane.

In another preferred embodiment, a modified polyetherurethane material can be used in the practice of the present invention. The preferred polyetherurethane material will be referred to as F2000-HEDP. The base polyetherurethane (PEU F-2000) is synthesized from diphenylmethane -4,4'-diisocyanate (MDI), a 1,4-butanediol (BD) chain extender, and a polytetramethylene oxide of MW 2000 (PTMO-2000 from Dupont) at a reactant ratio of MDI:BD:PTMO$_{MW=2000}$ 5:3:2, 1.7% hydroxyl excess. The phosphonate modified PEU is synthesized according to U.S. Pat. No. 5,436,291 whose entire contents are hereby incorporated by reference. Typically, ethanehydroxydiphosphonate (EHDP or HEDP sold by Monsanto as Dequest 2010) is first reacted with a polyfunctional epoxide (Decanol 521-Nagasi Chemicals, Osaka, Japan), and then with the PEU. The ratio of EHDP or HEDP to total final polymer varied from 100 to 400 nmol/mg.

Another material that can be used in the practice of the present invention is a polyurethane polymer known as Biomer and sold by Ethicon Corp of Sommerville, N.J. Another material is natural material such as bovine pericardium tissue.

The valves of the invention are typically of the stent type but could also be stentless. The stent material is typically hard polymer such as high durometer polyurethane, polyacetel, or other suitable compounds with a high degree of stiffness. Additionally, the valves have a plurality of leaflets. By a plurality of leaflets applicant means two or more leaflets. In a preferred embodiment, the heart valves of the present invention are of the tri-leaflet design. The valves of the present invention are fabricated as follows: The polymer material e.g., the silicone rubber or the polyetherurethane is dissolved in a solvent such as 1,1,1-trichloroethane and an amide such as dimethylacetamide or dimethylformamide, respectively. The typical concentration of polymer in solution is 10%, w/v in solvent. The concentration of course can be varied depending on the solubility and MW of the polymers, however typically the concentration range is 8–14% polymer, w/v in the solvent. Following dissolution of the polymer, a hard polymer stent is repeatedly dipped into the polymer solution and dried in an environment of 15–25% humid air. The valves are preferably dried in 20% humid air. The coated stent is then placed over a leaflet mandrel, which is dipped several times into the solution to provide heart valves leaflfets of the desired thickness. The desired thickness of course will depend on the number of times that the leaflet mandrel is dipped. Of course, the valve may be formed by injection or compression molding, or by thermo forming processes.

The heart valves of the present invention are coated with organic molecules that impart resistance to in-vivo calcification and resistance to in-vivo thrombus formation. The organic coatings that are utilized in the practice of the present invention are photochemically applied. The preferred coatings are described in U.S. Pat. Nos. 4,979,959; 5,002,582; and 5,263,992, including all abandoned, continuing, and divisional applications, whose entire contents are incorporated here by reference. Briefly, the coatings of the present invention are derived from a compound of the formula

X-Y-Z wherein X is a photochemically reactive group capable upon activation of bonding to the surface of the heart valve; Y represents nothing or a relatively inert, noninterfering skeletal moiety joining group X and is resistant to cleavage in aqueous physiological fluids and Z represents a functionally active moiety or biocompatible agent. The noninterfering skeletal moiety of Y may include an alkyl chain ($C_1$–$C_{10}$) or PEO (MW=200–1450). The photochemically reactive group X is selected from the group consisting of aryl, alkyl, and acyl azides, azidoformates, sulfonylazides, phosphoryl azides, diazo compounds, diazirines, ketenes, and aromatic ketones. The preferred photochemically reactive group is an aromatic ketone such as the benzophenone moiety having functionality such as carboxyl groups, amino groups or other reactive functionality to bond to the Y or Z group.

The Z group is selected from the group consisting of a $C_1$–$C_{18}$ alkylene group, a carboxy functionalized $C_1$–$C_{18}$ group, a mucopolysacharide, a polyoxyethylene, a residue of a vinyl polymer or a polypeptide. The preferred Z groups is a moiety selected from the group consisting of a fatty acid, hyaluronic acid, polyoxyethylene, heparin and vinylpyrrolidone. The preferred surface modifiers of the present invention include photoreactive fatty acid (FA-1) (Reagents #2036, 2040, and 2041 from SurModics, Inc., Eden Prairie, Minn.), Photoreactive poly (vinyl pyrrolidone) (Photo PVP, SurModics Product Code PV05), Photoreactive hyaluronic acid (HA-1) (SurModics Reagents #28 and #54), Photoreactive alkyl $C_{16}$ (SurModics Reagent #3008), and Photoreactive PEO (SurModics Reagent 1001), all provided by SurModics, Inc. of Eden Prairie, Minn.

In the process of applying the coatings of the present invention, sometimes it is useful to use a photoprimer known as SurModics Product Code PRO1 tetrakis (4-benzoylbenzyloxymethyl) methane. The above coatings are typically applied by dipping the heart valve including the leaflets into the coating solution and then activating photolytically. Typically, prototype polymer valves are constructed using leaflets fabricated of the above preferred polymers. The photo-fatty acid reagent or other photoactive reagent was dissolved to 5.0 mg/ml in isopropanol. After 5 min plasma (in an inert gas i.e, Argon) treatment, the valves were incubated 1 min with photoreagent solution at room temperature, air dried, and illuminated 3 min at 2 mW/cm$^2$ intensity within the 335–345 nm window using a dual Dymax model PC-2 light sources with 365 nm peak intensity bulb. The procedure can be repeated as desired to achieve the thickness.

In the case of the photopolyvinylpyrrolidone reagent the PVP reagent was dissolved to 5.0 mg/ml in water. After 5 min Argon plasma treatment, the valves were incubated 1 min with photo-PVP solution at room temperature, air dried, and illuminated 3 min. The procedure can also be repeated several times to produce modified substrates. The above coating materials provide the heart valves with a coating that imparts calcification resistance and resistance to thrombus formation.

Although applicant does not wish to be bound to any mechanistic theories regarding how the coatings of the present invention work, they are believed to be bonded to the surface either by covalent interactions or non-covalent interactions or both including Van der Waals interactions.

The surface modified heart valves including the surface modified leaflets of the present invention are tested using the Ovine mitral model as described by E. D. Irwin et al in "Long term evaluation of prosthetic mitral valves in sheep", *J. Invest. Surgery.*, 6, 133–141 (1993). Briefly, Juvenile sheep, 30–35 Kg in weight to insure good valve size fit were selected. The native mitral valve was excised and replaced with the prosthetic polymer valves of the present invention. The valves are retrieved 150 days after implant, then fixed in 10% neutral buffered formalin and subjected to histological evaluation. The valves were typically radiographed, photographed and examined visually for the presence of abnormalities such as endocarditis, and to determine leaflet condition and valve functionality. The histological sections were prepared in glycol methacrylate and stained in hematoxylin and eosin, and von Kossa stain for calcium and phosphate as described by F. J. Schoen et al "Calcification of bovine pericardium used in cardiac valve bioprostheses. Implications for the mechanisms of bioprosthetic tissue mineralization", *Am. J. Pathol.*, 123, 134–145 (1986).

The surface modified polymer valves of the present invention having photo-fatty acid or photohyaluronic acid coatings were implanted in the mitral position of ovine subjects and retrieved after the nominal 150 days implant. Upon gross examination, it was apparent that thrombus accumulation on the surface modified valves and the calcification deposits were less than that observed on the unmodified valves.

The present invention is further illustrated by the following Examples which are not intended to be limiting. It is to be understood by those skilled in the art that modifications and changes can be made thereto without departing from the spirit and scope of the invention.

EXAMPLE 1

The following describes a method for dip cast fabrication of high performance silicoe rubber (SR) polymer heart valves.

The materials used in fabrication were as follows: High Purity Nitrogen Gas, compressed Oxygen Gas, Silicone Rubber (HP-100), Isopropanol, Isoplast 202 (Dow Chemical, Midland, Mich.), and 1,1,1,trichloroethane (TCE).

Solution Preparation: 10% (w/w) solution of SR (HP-100) in TCE was prepared. Also, a 200 ml of a 12% (w/w) solution of SR in TCE and a 200 ml of a 3% (w/v) ivory soap/water solution was prepared.

Stent Preparation: The stent was washed in isopropanol using an ultrasonic water bath. Using forceps, the stent was placed into the oxygen plasma chamber, where the stent was plasma etched for 1 hr. The stent was then removed from the plasma chamber and immediately submerged in the 10% (w/w) SR/TCE solution for 10 minutes. Finally the stent was removed to allow excess solution to run off.

Stent Dip Casting: The stent was placed on a 3-prong plastic valve stent holder, the holder attaching along the annulus of the stent so that stent tips are dipped first. The stent was then dipped into the 12% solution of SR/TCE to the base of the stent tips a sufficient number of times to fit snugly over the leaflet mandrel. After each dip the stent was allowed to rotate dry in the controlled nitrogen environment. Seven dips is normally sufficient, however, dip number varies based on stent width and solution concentration (concentration changes due to evaporation).

Valve Dip Casting: All aluminum mandrel surfaces were first cleaned using water or isopropanol and a non-abrasive cloth or towel. The leaflet mandrel was dip coated by hand with the releasing agent (3% ivory soap/water solution) and allowed to rotate in a dry nitrogen environment for at least 30 min. The stent was then placed over the leaflet mandrel, and dipped into the 12% solution of SR in TCE. Dip the leaflet mandrel a predetermined number of times to produce the desired leaflet thickness. Between each dip the mandrel was rotated dry in the dry nitrogen environment. Several dips in a new 12% solution produced the desired leaflet thickness. As solution evaporates, leaflet thickness varied based on concentration. After the last dip both the stent and the mandrel were allowed to dry for 1 hr. The valve was cured for 4 hr. at 177° C., then coated. Water was applied to remove excess releasing agent.

EXAMPLE 2

This example shows the photochemical surface modification of polymeric valve leaflet substrates. The following substrate polymers are used: High performance silicone rubber (HP-100, Dow Coming, Midland Mich.) and Phosphonate modified poly(ether urethane) (PEU) (PU-1, made by Dr. Robert J. Levy, University of Michigan, Ann Arbor, Mich.).

Coating leaflets using Photoreactive Fatty Acid (Photo FA-1, SurModics Reagent #2040):

Prototype polymer valves were constructed using leaflets fabricated of the above test polymers. Photo FA-1 reagent was dissolved to 5.0 mg/ml in isopropanol. After min plasma (in an inert gas i.e, Argon) treatment, the valves were incubated 1 min with Photo FA-1 solution at room temperature, air dried, and illuminated 3 min at 2 mW/cm$^2$ intensity within the 335–345 nm window using a dual Dymax model PC-2 light sources with 365 nm peak intensity bulb. The procedure was twice repeated to obtain 3× modified substrates.

Coating leaflets using Photoreactive Poly (vinyl pyrrolidone) (Photo PVP, SurModics Product Code PV(05):

The Photo PVP reagent was dissolved to 5.0 mg/ml in water. After 5 min Argon plasma treatment, the valves were incubated 1 min with photo-PVP solution at room temperature, air dried, and illuminated 3 min. The procedure was once repeated to obtain 2× modified substrates.

Coating valve leaflets with Photoreactive hyaluronic acid (Photo HA-1, SurModics Reagent #28):

Photo HA-1 reagent was dissolved to 10.0 mg/ml in water. Valves were Photo PVP modified, then incubated 1 min with photo HA-1 solution at room temperature, air dried, and illuminated 4 min. The procedure was once repeated to obtain 2× modified substrates.

EXAMPLE 3

The following example illustrates surface modified silicone valves.

The substrate polymer used is a high performance silicone rubber (SR) (HP-100, from Dow Corning, Midland Mich.). The reagents used are: Photo reactive fatty acid (Photo FA-2), SurModics Reagent #2041 and Photo-reactive poly (vinyl pyrrolidone) designated as PV05.

Coating silicone rubber leaflets with Photo FA-2: The Photo FA-2 modification procedure is identical with that used in Example 2 except that Photo FA-2 solution was heated to 55° C. prior to incubation.

Coating silicone rubber leaflets with Photo PVP: The Photo PVP reagent was the same one used in Example 2. The Photo PVP reagent was dissolved to 3.0 mg/ml in water. After 5 min Argon plasma treatment, valves were immersed with stent posts up in a beaker containing PV05, 3 mg/ml in water, illuminated 45 s, and placed with stent posts down in a second beaker containing PV-05. The valve was again illuminated 45 s rinsed in water, then illuminated 2 min wet-to-dry while rotating between dual lamps.

Further modification with Photo-primer Photo-tetrakis (4-benzoylbenzyloxymethyl)methane, SurModics product code PR01): After initial PVP modification, valves were immersed in PR01/PVP, 0.15/10 mg/ml isopropanol solution, withdrawn at 0.05 cm/s, air dried, humidified, illuminated 2 min, rotated, illuminated 1 min, rotated, and illuminated 30 s.

Coating of valve leaflets with photoreactive hyaluronic acid (Photo HA-2, SurModics Regent #54):

The photo HA-2 was dissolved to 2.5 mg/ml in 50%, v/v, isopropanol/water. After Photo PVP modification, valves were immersed in Photo HA:2.5 mg/ml in isopropanol/water, with stent posts up, withdrawn at 0.05 cm/s, air dried, humidified, illuminated 2 min, rotated, illuminated 1 min, rotated, and illuminated 30 s. The valve was then immersed in Photo HA-2 solution with stent posts down, withdrawn at 0.01 cm/s, air dried, humidified, illuminated 2 min, rotated, illuminated 1 min, rotated, and illuminated 30 s. The latter was twice repeated to obtain 4x modified substrates.

EXAMPLE 4

The present example illustrates how to simulate in vitro the in vivo calcification of elastomeric materials under conditions of equivalent dynamic stress. The polymers used are: F2000/4074 (a polyether urethane coated with a silicone urethane copolymer), F2000-HEDP:PU2, Biomer and HP100. The PU2 modifier in F2000-HEDP:PU2 specifies a formulation of 1.0 mg HEDP per 1.0 g F2000. Testing in plasma and in metastable calcium phosphate solution was done. The samples were inspected visually and by Fourier transform infrared spectroscopy (FTIR) analysis. Elemental analysis was done by inductively coupled plasma (ICP)/atomic emission spectroscopy (AES) and molecular weight (MW) distribution analysis was done by gel permeation chromatography (GPC). Samples were also examined by FTIR using attenuated total reflectance mode (FTIR/ATR). Each specimen was blown dry with warm air. Dryness was verified by inspection of the FTIR spectra in areas where water appears. An internal reflection element of germanium at an incident angle of 45°, open aperture, 4.0 resolution, and 16/sample scanning were used Samples were to be incubated for 8 week under constant 38 psi cyclic stress. However, because little deposit was evident after 8 week incubation with plasma, polymers were stressed an additional 2 week at 38 psi. As little deposit was evident after 10 week, samples were stressed an additional 2 week at 75 psi. Based upon the results with plasma, samples were incubated with metastable calcium phosphate solution for 8 week at 38 psi, then 2 additional week at 75 psi.

For samples incubated with metastable calcium phosphate solution, adherent material was removed from the surface by 5 min agitation in 5%, v/v nitric acid solution at room temperature. Each sample was air dried and weighed to ±0.0001 g. Each polyetherurethane (PEU) specimen was digested in 2.5 ml concentrated nitric acid at 210 W microwave power. The silicone samples were digested similarly in two steps. Samples were first microwaved in a solution of 1 ml concentrated hydrofluoric/1 ml concentrated sulfuric acid, then again after addition of 3 ml nitric.

For samples incubated with plasma, adherent material was removed from the surface by 24 hr incubation with 0.6%, w/w, pepsin solution at 37° C., pH=1.8. No nitric acid rinse was used. Upon removal from the pepsin solution, each specimen was water rinsed, air dried, and weighed. Polymer samples were also similarly digested.

Samples were also analyzed by GPC for changes in MW distribution. Samples dissolved to 1%, w/v, in dimethylacetamide (DMAC). Solutions were filtered through a 0.45 mm syringe filter. 200 ml, dissolved polymer samples were fractionated serially through two Shodex columns ($10^3$, $10^4$). The column temperature was maintained at 80° C.

Visual observations for samples incubated with plasma: After 12 week incubation of the samples in plasma, the right front and left rear samples were removed the test unit. Little deposit was present on any of the samples, but more deposit was visible on the unmodified PEU urea (PEUU) samples (Biomer) than on the modified PEU (F2000-HEDP), the silicone-urethane (F2000/4074), or the silicone rubber (HP100).

After an additional 2 week incubation of the samples in plasma at higher cyclic strain, the remaining samples were removed from the units. As shown in the FIGS. 1 through 4, more deposit was present on Biomer and F2000-HEDP samples than on F2000/4074 or HP100 polymers. Less deposit was observed in the high stress center than in the low stress ends of the HP100 samples. In general, deposits were tightly adherent and rigid in the center of the dogbone.

FTIR spectra of the material adherent to samples stressed in plasma are similar to that of beta-tricalcium phosphate, a hydroxyapatite precursor. Strong phosphate peaks at 1030 $cm^{-1}$ suggest the presence of immature hydroxyapatite like crystals and characteristic peaks at 1530 & 1650 $cm^{-1}$ suggest the presence of protein in the matrix.

FTIR analysis of polymeric samples after removal of mineral: FTIR spectra of polymers stressed in plasma analyzed after removal of mineral deposits provided no evidence for bulk chemical degradation of either HP-100, 4074, F2000-HEDP. In contrast, spectra of Biomer and BPS-215 samples showed decreased intensity relative to controls of the peak at 1109 $cm^{-1}$ (indicative of soft segment ether), suggesting degradation of polymer soft segment. Further, a new peak is evident at 1632 $cm^{-1}$, suggesting increased urea carbonyl functionality. Chemical changes in BPS-215 were more extensive than in Biomer. No new peak at 1174 $cm^{-1}$ (indicative of ester functionality) appears in the spectra. In contrast such a new peak does appear in the spectrum of a polyetherurethane implanted stressed and caged, subcutaneously in rats reflecting the difference between the in vitro, blood plasma, and in vivo, subcutaneous cage environments. However, both studies demonstrate the instability of the PEU soft segment, and this study demonstrates that stress of PEUU in plasma can effect changes in the bulk chemistry of the polymer.

Elemental analysis of mineral adherent to polymeric samples: Calcium and phosphorus content of the mineral adherent to the polymers was measured by ICP/AES. An attempt was made to differentiate between calcium internalization and externalization by analyzing both the mineral-lipid-protein layer and the polymers themselves. The adherent layer was first dissolved from the polymer by incubation in acidic enzyme solution, then analyzed for solubilized mineral (externalized mineral). The polymer was then dissolved in an acid solution, which was then analyzed for solubilized mineral (internalized mineral).

The present Example demonstrates that less mineral was adherent to HP-100 than to the other polymers stressed 14 weeks in plasma. Polymer mineralization appears to be an interfacial phenomenon. The deposits appear to be nucleated immediately subsurface or appear to be growing into the polymer. These results clearly demonstrate the causal relationship between polymer stress and polymer mineralization.

High performance silicone rubber (SR) (HP-100, Dow Corning, Midland Mich.), surface modified by photo-hyaluronic acid (HA), photo-poly(ethylene oxide) (PEO), photo-alkyl C16 (C16) and photo-fatty acid (FA) (all SurModics, Eden Prairie Minn.), as well as unmodified SR, were cyclically stressed in vitro in heparinized bovine plasma supplemented with potassium phosphate and calcium chloride. Polymers were characterized by ESCA and DCA. Adherent mineral was analyzed by ICP/AES. Surface modification by Photo FA-1, C16, HA-1, and PEO increased calcification of SR, but not to the level previously observed with PEU.

Cast SR (HP-100, lot HX023001, Dow Corning, Midland Mich.) samples were surface modified as shown in Examples 2 and 3. Table I shows the samples tested:

TABLE IV

Surface Modified Silicone Rubber Samples Tested

| Code | Modification | Source |
|---|---|---|
| SR | none (control) | Dow Corning (Midland MI) |
| SR/HA-1 | Photo-hyaluronic acid | SurModics (Eden Prairie MN) |
| SR/C16 | Photo-alkyl C16 | SurModics (Eden Prairie MN) |
| SR/FA-1 | Photo-fatty acid | SurModics (Eden Prairie MN) |
| SR/PEO | Photo-PEO | SurModics (Eden Prairie MN) |

Surface characterization of polymers by DCA: Dynamic contact angles of unmodified and surface modified SR samples appear in Table II (SR samples were incubated with photo-ligand, but prior to exposure of the samples to UV light were masked to prevent photochemical reaction. All samples were rinsed with isopropanol, then water prior to contact angle measurement.

TABLE II

Dynamic Contact Angles Of Unmodified and Surface Modified SR Samples

| PHOTO-LIGAND | EXPOSED TO UV? | $\theta_{adv}$ | $\theta_{rec}$ |
|---|---|---|---|
| HA-1 | YES | 48.4 ± 1.93 | 9.82 ± 0.28 |
| PEO | YES | 69.5 ± 1.50 | 25.7 ± 3.21 |
| FA-1 | YES | 77.8 ± 0.38 | 12.8 ± 0.07 |
| HA-1 | NO | 52.7 ± 0.89 | 23.2 ± 0.20 |
| PEO | NO | 66.9 ± 1.67 | 17.7 ± 0.28 |
| FA-1 | NO | 70.8 ± 0.63 | 20.1 ± 0.14 |
| NONE | NO | 117.0 ± 0.60 | 79.7 ± 0.70 |

These data confirm photochemical modification of the SR substrate.

Elemental analysis of mineral adherent to polymeric samples: Calcium and phosphorus content of the mineral adherent to the polymers was measured by ICP/AES. No attempt was made to differentiate between calcium internalization and externalization. The adherent layer and the polymer substrate were dissolved together in acid solution, which was then analyzed for solubilized mineral. A tabular summary of calcium and phosphorous incorporation by polymers cyclically stressed in plasma, as well as the Ca/P ratio, appear in Tables III, IV and V respectively.

TABLE III

Calcium Content Of Interfacial Mineral Adherent to Surface Modified SR Stressed Up to 8 Week in Plasma

| | | Interfacial calcium, wt % incubation time, week | | | | | |
|---|---|---|---|---|---|---|---|
| | Surface | 4 | | 6 | 8 | | |
| Subst. | Modification | n1 | n2 | n1 | n2 | avg | sdv |
| SR | none | 0.09 | 0.10 | 0.09 | 0.08 | 0.09 | 0.01 |
| SR | FA-1 | 0.0 | 0.14 | 0.17 | 0.28 | 0.23 | 0.08 |
| SR | C16 | 0.20 | 0.51 | 0.54 | NA | 0.54 | 0.0 |
| SR | HA-1 | 0.27 | 0.29 | 0.08 | 0.13 | 0.11 | 0.04 |
| SR | PEO | 0.38 | 0.39 | 0.40 | 0.21 | 0.30 | 0.14 |

TABLE IV

Phosphorous Content of Interfacial Mineral Adherent to Surface Modified SR Stressed up to 8 Week in Plasma

| | | Interfacial phosphorous, wt % incubation time, week | | | | | |
|---|---|---|---|---|---|---|---|
| | Surface | 4 | | 6 | 8 | | |
| Substrate | Modification | n1 | n2 | n1 | n2 | avg | sdv |
| SR | none | 0.07 | 0.07 | 0.07 | 0.05 | 0.06 | 0.01 |
| SR | FA-1 | 0.0 | 0.09 | 0.10 | 0.17 | 0.14 | 0.05 |
| SR | C16 | 0.13 | 0.28 | 0.42 | NA | 0.42 | 0.00 |
| SR | HA-1 | 0.18 | 0.16 | 0.05 | 0.06 | 0.05 | 0.01 |
| SR | PEO | 0.21 | 0.23 | 0.23 | 0.14 | 0.19 | 0.06 |

TABLE V

Ratio of Calcium to phosphorous (CA/P) in Interfacial Mineral Adherent to Surface Modified Sr Stressed up to 8 Week in Plasma

| | | Interfacial calcium/phosphorous ratio incubation time, week | | | | | |
|---|---|---|---|---|---|---|---|
| | Surface | 4 | | 6 | 8 | | |
| Substrate | Modification | n1 | n2 | n1 | n2 | avg | sdv |
| SR | none | 1.41 | 1.43 | 1.36 | 1.73 | 1.55 | 0.26 |
| SR | FA-1 | 1.65 | 1.55 | 1.66 | 1.64 | 1.65 | 0.01 |
| SR | C16 | 1.62 | 1.83 | 1.29 | NA | 1.29 | 0.00 |
| SR | HA-1 | 1.53 | 1.85 | 1.69 | 2.18 | 1.93 | 0.35 |
| SR | PEO | 1.81 | 1.69 | 1.75 | 1.46 | 1.60 | 0.21 |

Interfacial phosphorous measurement was consistent with interfacial calcium measurement. Ca/P ratios (Table V) were generally near 1.5, compared with 1.0 for calcium phosphate dihydrate $(CaHPO_4 \times 2H_2O)_6$, 1.72 for octacalcium phosphate $(Ca_8H_2(PO_4)_6)$, and 2.15 for hydroxyapatite $(Ca_5(PO_4)_3OH)$. Surface modification with Photo FA-1, HA-1, C16, and PEO increased calcification of SR, but not to the level previously observed with Biomer. Interfacial mineralization, i.e., accumulation of calcium and phosphorous at the polymer surface, of SR increased upon surface modification, in increasing order: Photo HA, FA, PEO, C16.

EXAMPLE 5

Twelve valves of the present invention having leaflets of high performance silicone rubber, surface modified with photo-fatty acid (FA-1) or photohyaluronic acid (HA-1) coatings (one sample group comprised 6 valves surface modified with HA-1, the other group comprised 6 valves surface modified with FA-1) were implanted in the mitral position of ovine subjects. Three valves from each sample group were successfully retrieved after a nominal 150 days implant (HA-1 valves were designated JFV61, JFV62, and JFV64; FA-1 valves were designated JFV66, JFV67, and JFV69) and compared with control valves having unmodified leaflets of high performance silicone rubber. Upon gross examination, it was apparent that thrombus accumulation and visible calcification on and in the surface modified valve leaflets were less than that observed on the unmodified valves. See pictures through 5 through 7.

As shown in the pictures, small thrombi were observed present in the commisures, and red, thrombus-like adhesions were observed at the outflow cuff-stent interface of most valves and is thought to be related to valve design. Also, some of the valves, most notably JFV61 and JFV 62, had a suture looped around one stent post, which prevented leaflet coaptation and resulted in tissue depositing around the looped stent post. Also, paravalvular leaks (due to improper seating of the valve) were noted in some of the valves, JFV62, JFV64, and JFV66. Generally white tissue encapsulated the sewing cuffs of the valves, and no intrinsic calcific deposits, and very little thrombus-like material is adherent to inflow and out flow aspects of the leaflets compared to the non-surface treated valves. The results of these and other animal studies show that the modification of both silicone rubber and polyetherurethane with hyaluronic acid (HA-1) resulted in decreased thrombus adhesion relative to the respective unmodified substrates.

Briefly, the testing is done using the Ovine mitral model as described by E. D. Irwin et al in "Long term evaluation of prosthetic mitral valves in sheep", *J Invest. Surgery.*, 6, 133–141 (1993). Briefly, Juvenile sheep, 30–35 Kg in weight to insure good valve size fit were selected. The native mitral valve was excised and replaced with the prosthetic polymer valves of the present invention. The valves are retrieved 150 days after implant, then fixed in 10% neutral buffered formalin and subjected to histological evaluation and chemical analysis.

EXAMPLE 6

In order to determine valve histopathology, a leaflet and sewing cuff section of each of the explanted valves of Example 5 were imbedded in paraffin. Sections were stained with hematoxylin and eosin (HE) for cellular detail and morphology, with Masson's trichrome (TRI) for collagen, with phosphotungstic acid and hematoxylin (PA-HE) for fibrin, and von Kossa (VK) for calcified mineral. The valve surface modified with HA-1 (i.e., JFV61, 62 and 64) confirmed that the sewing cuff was well healed, but showed an organizing thrombus present at the sewing cuff surface. JFV61 and JFV64 showed focal thrombus and/or calcification at the leaflet surface, which during gross examination was shown to be related to surgical complications. In a related study—move free of surgical complications, HA-1 modified leaflets showed no adherent thrombus. The valve surface modified with FA-1 (i.e., JFV64, 66, and 67) showed not only that the sewing cuffs were well healed, but also that the leaflets were free of adhesions.

EXAMPLE 7

To determine photoreagent retention by the surface modified valves, a second leaflet and sewing cuff section of the explanted valves of Example 5 were dissolved in 0.5 ml Soluene 350 (catalog number 6003038, Packard Instrument, Downers Grove, Ill.) at 55° C. for 1.5 hr, then 5.0 ml Hionic-Flour™ (Packard Instrument) liquid scintillant. The radioactivity retained by each leaflet and sewing cuff was measured using the tritium window of a beta radiation counter. The reagent retention for the HA-1 and FA-1 valves was 27.8% and 13.8% respectively. The results of these tests showed that surface modification did not affect leaflet calcification, and the results confirmed that surface modified valves had decreased thrombus adhesion to leaflets without effecting leaflet calcification.

EXAMPLE 8

Another leaflet and sewing cuff section was removed from each explanted valve of Example 5, and measured for intrinsic calcium and phosphorous contents using atomic absorption spectroscopy. These results were compared with the calcium contents of (1) a five month implant of a bioprosthetic valve (Hancock Porcine Valve, Medtronic, Minneapolis, Minn.) (276 $\mu$g calcium/mg dry tissue) and (2) a five month implant of unmodified high performance silicon rubber valve prosthesis (1.7 $\mu$g calcium/mg dry tissue). The results showed that the intrinsic calcium content of the surface modified valve leaflets (both HA-1, and FA-1) was lower than unmodified bioprosthetic control, and not statistically different than the unmodified silicone rubber control. These results show that surface modification did not negatively affect intrinsic leaflet calcification.

It will be apparent from the foregoing that many other variations and modifications may be made regarding the biocompatible heart valves described herein, without departing substantially from the essential features and concepts of the present invention. Accordingly, it should be clearly understood that the forms of the inventions described herein are exemplary only and are not intended as limitations on the scope of the present invention as defined in the appended claims.

What is claimed is:

1. A method for reducing calcification and thrombus formation in a biocompatible heart valve comprising a polymer selected from the group consisting of silicone rubbers, polyurethane, and polyetherurethane, said method comprising:

coating, prior to implantation, said heart valve including its leaflets with a coating derived from a compound of the formula:

X-Y-Z wherein X is a photochemically reactive group capable upon activation of bonding to the surface of the heart valve, Y represents nothing or a relatively inert, non-interfering skeletal moiety joining groups X and Z and is resistant to cleavage in aqueous physiological fluids, and Z is a fatty acid moiety, said coating being effective to reduce calcification and thrombus formation after implantation.

2. A biocompatible heart valve comprising:

a stent defining a blood flow path; and a plurality of leaflets comprising a polymer selected from the group consisting of silicone rubber, polyurethane, and polyetherurethane, said leaflets having an applied surface coating effective to render said heart valve resistant to in vivo pathologic thrombus formation and in vivo pathologic calcification, said coating being derived from a compound of the formula

X-Y-Z wherein X is a chemically reactive group capable upon activation of bonding to the surface of the heart valve; Y represents nothing or a relatively inert, noninterfering skeletal moiety joining groups X and Z and is resistant to cleavage in aqueous physiological fluids, and Z is a fatty acid moiety.

3. A method for reducing calcification and thrombus formation in a biocompatible heart valve comprising a polymer selected from the group consisting of silicone rubbers, polyurethane, and polyetherurethane, said method comprising:

providing a first coat, prior to implantation, to said heart valve including its leaflets, of a first coating derived from a compound of the formula:

X-Y-Z wherein X is a photochemically reactive group capable upon activation of bonding to the surface of the heart valve, Y represents nothing or a relatively inert, noninterfering skeletal moiety joining groups X and Z and is resistant to cleavage in aqueous physiological fluids, and Z is a polyvinylpyrrolidone moiety, and providing a second coat, prior to implantation, to said heart valve including its leaflets, of a second coating comprising a hyaluronic acid moiety coupled to said polyvinylpyrrolidone moiety.

4. A biocompatible heart valve comprising:

a stent defining a blood flow path; and a plurality of leaflets comprising a polymer selected from the group consisting of silicone rubber, polyurethane, and polyetherurethane, said leaflets having an applied surface coating effective to render said heart valve resistant to in vivo pathologic thrombus formation and in vivo pathologic calcification, said applied surface coating comprising:

a first coating derived from a compound of the formula

X-Y-Z wherein X is a chemically reactive group capable upon activation of bonding to the surface of the heart valve; Y represents nothing or a relatively inert, noninterfering skeletal moiety joining groups X and Z and is resistant to cleavage in aqueous physiological fluids, and Z is a polyvinylpyrrolidone moiety; and a second coating comprising a hyaluronic acid moiety coupled to said polyvinylpyrrolidone moiety.

* * * * *